(12) United States Patent
Hannula et al.

(10) Patent No.: US 7,440,789 B2
(45) Date of Patent: Oct. 21, 2008

(54) ELECTRODE STRUCTURE FOR MEASURING ELECTRICAL RESPONSES FROM THE HUMAN BODY

(75) Inventors: Henri Hannula, Helsinki (FI); Matti Aho, Espoo (FI); Marko Ollikainen, Helsinki (FI)

(73) Assignee: Nexstim Oy, Helsinki (FI)

( * ) Notice: Subject to any disclaimer, the term of this patent is extended or adjusted under 35 U.S.C. 154(b) by 0 days.

(21) Appl. No.: 10/579,832

(22) PCT Filed: Nov. 16, 2004

(86) PCT No.: PCT/FI2004/000687

§ 371 (c)(1),
(2), (4) Date: May 17, 2006

(87) PCT Pub. No.: WO2005/048837

PCT Pub. Date: Jun. 2, 2005

(65) Prior Publication Data

US 2007/0106141 A1    May 10, 2007

(30) Foreign Application Priority Data

Nov. 18, 2003    (FI) .................................. 20031677

(51) Int. Cl.
*A61B 5/04* (2006.01)
(52) U.S. Cl. ....................... 600/383; 600/396
(58) Field of Classification Search ................. 600/383, 600/396
See application file for complete search history.

(56) References Cited

U.S. PATENT DOCUMENTS

| | | | | |
|---|---|---|---|---|
| 3,170,459 A | * | 2/1965 | Phipps et al. | 600/391 |
| 3,469,577 A | * | 9/1969 | Kater | 600/383 |
| 3,580,240 A | * | 5/1971 | Cosentino | 600/392 |
| 4,040,412 A | * | 8/1977 | Sato | 600/391 |
| 4,051,842 A | * | 10/1977 | Hazel et al. | 600/391 |
| 4,323,076 A | * | 4/1982 | Sams | 600/383 |
| 4,537,198 A | * | 8/1985 | Corbett | 600/383 |
| 4,580,572 A | | 4/1986 | Granek et al. | |
| 4,773,424 A | | 9/1988 | Inoue et al. | |
| 5,365,935 A | | 11/1994 | Righter et al. | |
| 6,067,464 A | | 5/2000 | Musha | |
| 6,091,977 A | | 7/2000 | Tarjan et al. | |
| 6,445,940 B1 | | 9/2002 | Gevins et al. | |
| 2003/0018366 A1 | | 1/2003 | Lamont | |

FOREIGN PATENT DOCUMENTS

| | | |
|---|---|---|
| JP | 4-067841 A | 3/1992 |
| WO | WO-00/27279 A1 | 5/2000 |

* cited by examiner

*Primary Examiner*—Lee S Cohen
(74) *Attorney, Agent, or Firm*—Birch, Stewart, Kolasch & Birch, LLP

(57) ABSTRACT

The invention relates to an electrode structure (10) for attachment to a more extensive measuring structure (11), in order to measure electrical responses from the human body. The electrode structure (10) includes a conductive electrode (1). According to the invention, the electrode (1) is shaped to be thin in the thickness direction of the electrode structure (10), and the electrode structure (10) is equipped with a hole (6) and the electrode (1) is located at the edge of the hole (6), in such a way that its longitudinal axis is essentially parallel to the plane of the measurement subject.

17 Claims, 2 Drawing Sheets

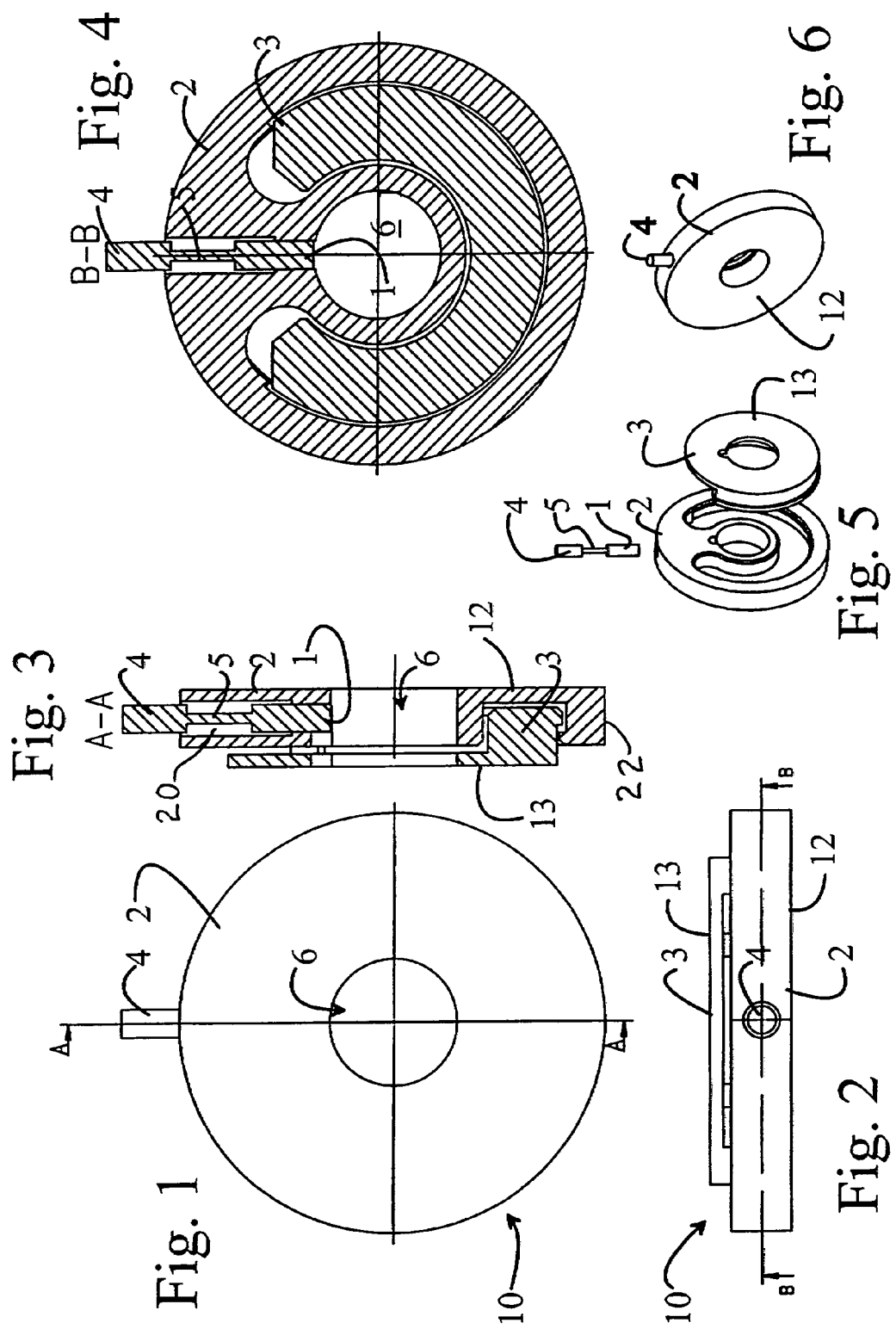

ELECTRODE STRUCTURE FOR MEASURING ELECTRICAL RESPONSES FROM THE HUMAN BODY

FIELD OF THE INVENTION

The present invention relates to an electrode structure for attachment to a more extensive measuring structure, in order to measure electrical responses from the human body.

The invention also relates to a measuring cap and a manufacturing method.

BACKGROUND OF THE INVENTION

According to the prior art, measurements made from the surface of the head in particular are made using silver electrodes for measuring electrical responses, for example, in TMS (transcranial magnetic stimulation) tests, in which an electromagnetic pulse is directed to the brain and the response it creates is measured using electroencephalograph (EEG) measuring equipment. In practice, electrically polarizing interfaces arise between the different materials in the silver electrodes according to the prior art and lead to interference signals that diminish the accuracy of the measurement.

The silver electrodes are chloridized, in an attempt to eliminate this phenomenon. Despite this measure, satisfactory results are not always achieved. As chloridization only affects the surface of the electrode, it is easily removed by wear or, for example, by unintentionally scratching the electrode. Chloridization must be performed regularly between measurements, leading to additional work and preventing continuous use of the electrodes.

In measurement caps according to the prior art, the electrode structures become detached easily during washing and are difficult to reattach.

DISCLOSURE OF THE INVENTION

The invention is intended to eliminate the defects of the state of the art disclosed above and for this purpose create an entirely new type of electrode structure.

The invention is based on the fact that the smaller the electrode, the smaller the electrical currents induced by a magnetic stimulation pulse, which fact is exploited in the invention by making the electrode thin in the thickness direction of the electrode structure, and by equipping the electrode structure with holes and locating the electrode at the edge of the hole, so that its longitudinal axis is essentially parallel to the plane of the measurement subject.

One preferred embodiment of the invention is, on the other hand, based on the realization that, if an electrode made from silver/silver-chloride is used, the electrode surface will also remain essentially unaltered, even if the electrode wears or is scratched, because the electrode consists throughout of the same material.

A third preferred embodiment of the invention is based on using small electrodes made from silver-chloride pellets, which can be installed in a measurement hood using a snap-fit attachment.

More specifically, the electrode structure according to the invention is characterized in that the electrode is shaped to be thin in the thickness direction of the electrode structure, and the electrode structure is equipped with a hole and the electrode is located at the edge of the hole, in such a way that its longitudinal axis is essentially parallel to the plane of the measurement subject.

The method according to the invention is, in turn, characterized in that the measuring electrode, which includes a silver/silver-chloride (Ag—AgCl) electrode and a silver lead connected to it, is attached to the measuring lead using an electrically conductive connection, for example, by soldering or crimping, forming the electrically conductive connection in such a way that the electrode does not touch the connection point, nor does the electrode touch magnetic material, nor is heat conducted to the electrode to such an extent that the sintered electrode structure will alter.

Considerable advantages are gained with the aid of the invention.

The solution according to the invention permits electrical responses to be measured during, or a short time after the magnetic pulses produced by the magnetic stimulators, typically after 1-5 ms, even after a powerful magnetic pulse, particularly if the solution according to the invention is used in conjunction with magnetic stimulation simultaneously with suitable EEG equipment.

The electrode structure according to the invention forms a stable electrical contact between the person being measured and the electrode. The attachment construction of the electrode is compact in size, thus permitting a TMS coil to be placed close to the surface of the head. The coil's effective distance is about 30 mm and the effective electrical field induced diminishes rapidly as the distance increases. The solution according to the invention permits the coil to be placed closer to the point it is wished to affect. With the aid of the invention, it is possible to create in the brain a TMS-induced electrical field that is typically 5-30% stronger than when using thicker electrode attachment constructions. The value of a 5-30% stronger electrical field is calculated from a distance difference of 2-3 mm, i.e. if the electrode's attachment were to be 2-3 mm thicker, the electrical field induced by TMS in the tissue would be correspondingly weakened.

According to one preferred alternative of the invention, the electrode structure 10 is entirely non-magnetic, i.e. the magnetization of all the structural materials is very small. For example, this is a great advantage and even an essential requirement in measurements made in connection with an MEG (magnetoencephalography) device. MEG compatibility is, in turn, a great advantage in laboratories and in applications, in which TMS and EEG, as well as MEG measurements are used. A non-magnetic structure is also very important if EEG measurements are made during MRI imaging (Magnetic Resonance Imaging), for example, in connection with FMRI (Functional Magnetic Resonance Imaging) tests. The electrode structure (10) is constructed in such a way that a special tool is needed to detach it, while, in addition, the construction protects the brittle silver-chloride electrode (1) from impacts, scratching, and wear.

The electrode structure according to the invention does not require chloridization, and thus interfaces that hamper measurements are not created in the electrode structure. When the electrode wears, its electrical properties remain unchanged.

In addition, the measurement point on the skin of the test person can be cleaned after the attachment of the electrode, as there is a sufficiently large hole (6) in the electrode structure.

The small size and compact shape of the electrode prevents the magnetic stimulation coil from inducing strong electromotor forces in the electrode and thus reduces the creation of eddy currents caused by the electrical fields.

In the following, the invention is examined with the aid of an example of an embodiment according to the accompanying drawings.

BRIEF DESCRIPTION OF THE DRAWINGS

FIG. 1 shows a bottom view of one electrode structure according to the invention.

FIG. 2 shows a side view of the electrode structure according to FIG. 1.

FIG. 3 shows a cross-sectional side view along the line A-A of the sensor according to the invention.

FIG. 4 shows a cross-sectional view along the line B-B of the electrode structure according to FIG. 2.

FIG. 5 shows an exploded perspective view of the electrode structure according to the invention.

FIG. 6 shows a perspective view of the electrode structure according to the invention.

DESCRIPTION OF THE INVENTION

Figure 7:
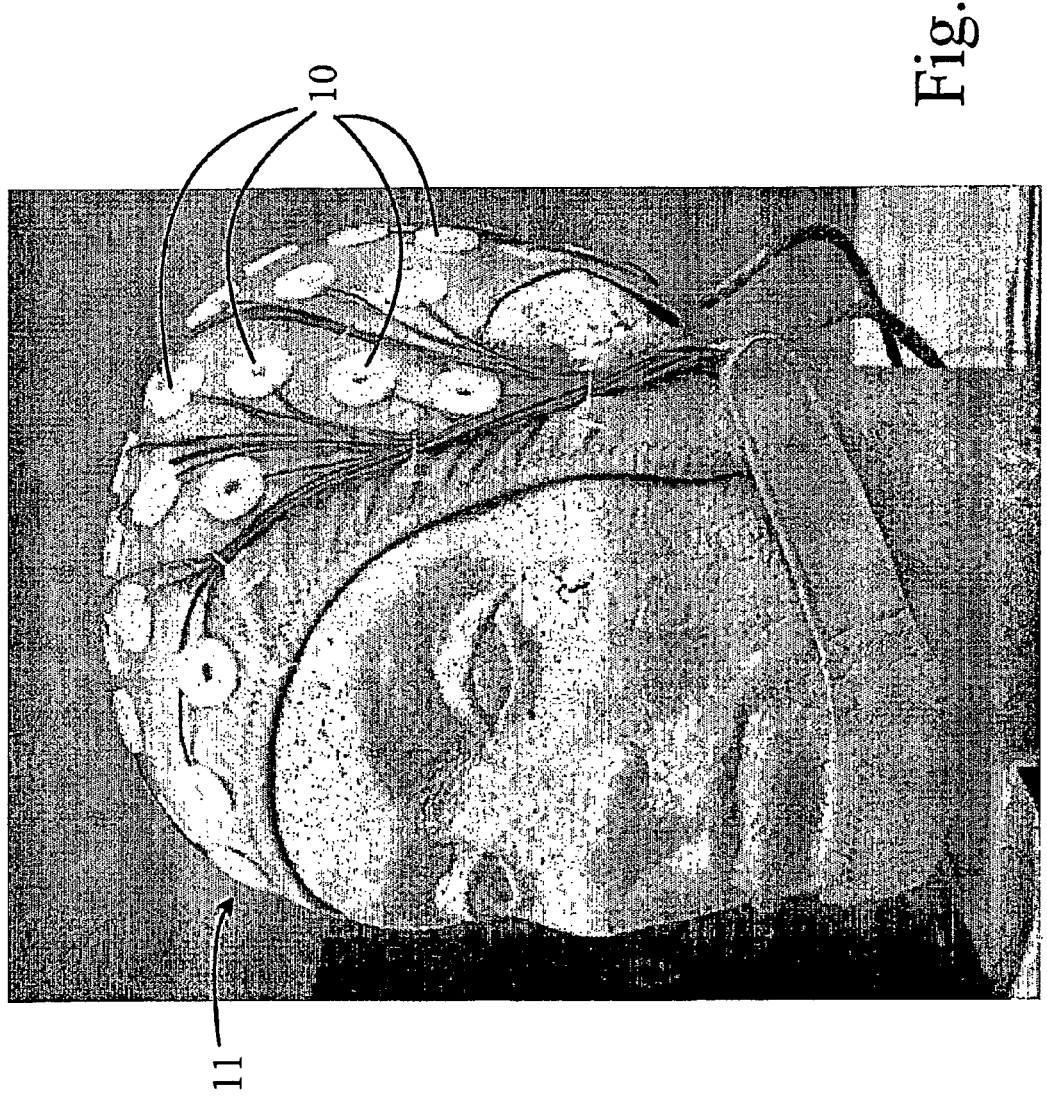
FIG. 7 shows a perspective view of electrode structures according to the invention, located on a measuring cap.

According to FIG. 1, the electrode structure according to the invention is examined from beneath, in other words, from the direction of the measurement subject. The electrode structure 10 includes a body piece 2, from which a measuring lead 4 protrudes. Electrical contact from the measurement subject, typically a person's scalp, to the electrode material, is formed through the hole 6, with the aid of an electrically conductive paste. According to the figure, the electrode structure 10 is essentially disc-shaped.

FIG. 2 shows the locking piece 3 connected to the body piece, by means of which the measuring cap described later is locked between the body piece and the locking piece. The locking piece 3 is located on the outer surface of the electrode structure, if the inner surface 12 is defined as the measuring surface, for example, the scalp.

FIG. 3 shows the construction of the measuring electrode 10 in greater detail. The measuring opening 6 extends through the entire structure and the piece 3 locks onto the body piece 2 with the aid of locking lugs. The electrode 1 made from silver/silver-chloride is positioned in an opening 20 formed in a peripheral surface 22 of the body piece 2 and which extends to the hole 6. As shown in FIG. 3, the electrode 1 is located at the very edge of the opening 6, thus forming a contact with the contact paste (not shown) in the hole 6. The electrode 1 is typically connected to the measuring lead 4 with the aid of a silver connector lead 5. The connection of the electrode 1, which the connector lead 5 also permanently forms part of, to the measuring lead 4 demands special measures, for example, there must be no silver/silver-chloride spatters in the silver wire 5 and the soldering of the measuring lead 4 and the silver wire must not touch the electrode 1, as the hot solder will melt the Ag—AgCl mass, which is made by sintering, and form an interface with it, which may, in turn, cause interference in the measuring situation. The electrode pellet 1 typically has a cylindrical shape, so that its longitudinal axis is parallel to the measuring surface. This alignment gives the electrode structure 10 a flat dimension, which is as small as possible, between the measuring surface 12 and the outer surface. The dimension of the electrode 1 in the thickness direction of the electrode structure 10 is, according to the invention, small, preferably less than 5 mm, and most preferably less than 2 mm. The term thickness of the electrode 1 refers to its dimension in the direction of the thickness of the electrode structure 10, in other words, for example, the left-to-right dimension in FIG. 3.

In this case, the term measuring situation refers, for example, to a measurement made after a stimulation pulse. Non-magnetic plastic, which is dry-machined, is used as the raw material for the plastic components 2 and 3. This is done, because the machining liquid used in the machining centre may contain magnetic materials, which would hamper measurement.

A particularly advantageous result is achieved, if a magnetization value less than that given below is achieved.

If the electrode construction is oscillated with an amplitude of about 5 cm at a distance of 3 cm from a sensor measuring the density of the magnetic flux, the peak value of the density of the magnetic flux caused by the oscillation of the electrode 10 should be less than 80 femtotesla in a shielded enclosure, in which there is a dc field of 30 nanotesla.

According to FIG. 4, the cross-section of the body piece 2 is essentially circular. A curved opening arrangement, in which the locking piece 3 is locked, is made in the circular piece 2. The electrode 1 extends to the hole 6 in the electrode structure. According to the figure, the brittle electrode 1 is tightly inside the body structure 2.

FIGS. 5 and 6 show a perspective view of additional details of the invention. Thus, the upper surface of the locking piece 3 is essentially annular in shape and forms a uniform flat surface 13 on the side opposite to the measuring surface 12.

According to FIG. 7, the electrode structures are placed at regular intervals in the cap 7 and the cap is placed around the skull.

The measuring leads of the measuring cap are wound into a tight, preferably spiral bundle, in order to reduce interference. In addition, according to a preferred embodiment of the invention, the earth and reference electrode leads of the measuring cap are wound tightly together, to reduce interference. Interference can be further reduced by running the measuring leads from the electrodes towards the front of cap 11.

Within the scope of the invention, the electrode structure can deviate from a disc-like shape and flat angular and elliptical shapes too are quite possible. The use of curved surfaces between the body 2 and locking 3 pieces achieves a more even locking effect.

According to one preferred embodiment of the invention, the electrode 1 of the electrode structure 10 is so small in size that a cross-section through any plane at all of the electrode 1 will have a surface area of less than 15 mm$^2$, more preferably of less than 4 mm$^2$.

The small size is important, in order to reduce the electrical field caused by induction and the eddy currents arising in the electrode 1.

The invention claimed is:

1. An electrode structure for attachment to a more extensive measuring structure, in order to measure electrical responses from the human body, the electrode structure comprising:
   a inner surface to contact with a measurement subject;
   an outer surface opposed a predetermined distance to the inner surface;
   a peripheral surface connecting the inner surface and the outer surface;
   a central opening in the inner surface extending through the outer surface;
   an opening in the peripheral surface extending though the electrode structure to meet the central opening; and
   an electrode fitted in the opening in the peripheral surface, the electrode having a measuring lead, an electrode pellet and a conductor connecting the measuring lead and the electrode pellet, an end of the electrode pellet being positioned where the opening in peripheral surface meets the central opening and a portion of the measuring lead extending beyond the peripheral surface.

2. The electrode structure according to claim 1, wherein the electrode is formed from silver/silver-chloride (Ag—AgCl), in order to form electrically stable interfaces between the measurement subject and the measuring electronics.

3. The electrode structure according to claim 2, wherein the conductor connecting the measuring lead and the electrode pellet is made of pure silver (Ag).

4. The electrode structure according to claim 2, wherein a thickness of the electrode structure anywhere between the inner surface and the outer surface is less than 5 mm.

5. The electrode structure according to claim 1, wherein a thickness of the electrode structure anywhere between the inner surface and the outer surface is less than 5 mm.

6. The electrode structure according to claim 5, wherein the thickness of the electrode structure anywhere between the inner surface and the outer surface is less than 2 mm.

7. The electrode structure according to claim 1, wherein the outer surface is configured to receive a locking piece and the electrode structure attaches to the more extensive measuring structure via the locking piece.

8. The electrode structure according to claim 7, wherein the outer surface has a curved opening and the locking piece locks into the curved opening.

9. The electrode structure according to claim 1, wherein a diameter of the central opening is in a range of between 2 nm and 4 mm.

10. The electrode structure according to claim 1, wherein the electrode pellet is cylindrical in shape and an axial direction in which the electrode pellet extends is essentially parallel to a plane of a subject being measured.

11. The electrode structure according to claim 10, wherein the electrode pellet has a cross-section along any plane perpendicular to the axial direction in which the electrode pellet extends with a surface area that is less than 15 mm$^2$.

12. The electrode structure according to claim 11, wherein the cross-section of the electrode pellet is less than 4 mm$^2$.

13. The electrode structure according to claim 1, wherein the electrode pellet is a sintered silver/silver-chloride mass (Ag—AgCl).

14. A measuring cap for measuring electrical responses from the human body, which measuring cap comprises:
   a cap configured to be place upon a human head; and
   one or more electrode structures according to claim 1 attached to the cap, wherein
   the measuring leads of the one or more electrode structures transmit measurement results to measuring equipment attached to the measuring leads.

15. The measuring cap according to claim 14, wherein the measuring leads are wound into a tight spiral bundle, in order to reduce interference.

16. The measuring cap according to claim 14, wherein the measuring leads include ground and reference electrode leads that are wound tightly to each other to reduce interference.

17. The measuring cap according to claim 14, wherein the measuring leads run from the electrode structures towards a front of the cap to reduce interference.

* * * * *